(12) United States Patent
Park et al.

(10) Patent No.: US 7,994,141 B2
(45) Date of Patent: Aug. 9, 2011

(54) COMPOSITIONS COMPRISING COMPOUNDS OF NATURAL ORIGIN FOR DAMAGED SKIN

(75) Inventors: Deok Hoon Park, Gyeonggi-do (KR);
Jong Sung Lee, Gyeong-do (KR);
Kwang sun Jung, Gyeonggi-do (KR)

(73) Assignee: Biospectrum, Inc., Gyeonggi-Do (KR)

( * ) Notice: Subject to any disclaimer, the term of this patent is extended or adjusted under 35 U.S.C. 154(b) by 16 days.

(21) Appl. No.: 12/093,233

(22) PCT Filed: Dec. 17, 2007

(86) PCT No.: PCT/KR2007/006604
§ 371 (c)(1),
(2), (4) Date: May 9, 2008

(87) PCT Pub. No.: WO2008/072941
PCT Pub. Date: Jun. 19, 2008

(65) Prior Publication Data
US 2010/0273729 A1    Oct. 28, 2010

(30) Foreign Application Priority Data
Dec. 15, 2006  (KR) .................. 10-2006-0128500

(51) Int. Cl.
*A61K 31/704*  (2006.01)
*A61K 31/70*  (2006.01)
(52) U.S. Cl. .................. 514/34; 514/25; 536/5; 536/4.1
(58) Field of Classification Search .................. 514/34, 514/25; 536/5, 4.1
See application file for complete search history.

(56) References Cited

FOREIGN PATENT DOCUMENTS

| | | | |
|---|---|---|---|
| DE | 3315463 A1 | * | 10/1984 |
| JP | 63253013 A | * | 10/1988 |
| JP | 09143087 A | * | 6/1997 |
| JP | 10120556 A | A | 5/1998 |
| JP | 10158142 A | * | 6/1998 |
| JP | 2001316665 A | * | 11/2001 |
| JP | 2004277354 A | * | 10/2004 |
| KR | 1019990057743 A | | 7/1999 |
| KR | 1020000042127 A | | 7/2000 |
| KR | 100411837 B1 | B1 | 5/2004 |

OTHER PUBLICATIONS

Harukuni et al., JP 10158142 A ; Jun. 16, 1998 (abstract sent).*
Alexa, DE 3315463 A1; Oct. 31, 1984 (Abstract sent).*
Murai, JP 2001316665 A; Nov. 16, 2001 (Abstract sent).*
Honda, JP 2004277354 A; Oct. 7, 2004 (Abstract sent).*
Yamamoto , JP 09143087 A; Jun. 3, 1997 (Abstract sent).*
Tsuboi et al., JP 63253013 A; Oct. 20, 1988 (abstract sent).*
Zita et al (Casopis Lekaru Ceskych (1955), 94, 203-8) (Abstract sent).*
English Translation of Abstract; Korean Publication No. KR-1019990057743(A); Applicant: Samsung Electronics Co., Ltd. Published: Jul. 15, 1999 (Abstract Only) (1 Pg).
English Translation of Abstract; Korean Publication No. KR-1020000042127(A); Applicant: Coreana Cosmetics, Co., Ltd. Published: Jul. 15, 2000 (Abstract Only) (1 Pg) .

* cited by examiner

*Primary Examiner* — Anna Jiang
*Assistant Examiner* — Michael C Henry
(74) *Attorney, Agent, or Firm* — Casimir Jones, S.C.

(57) ABSTRACT

The present invention relates to a skin-protecting composition for the damaged skin, comprising glycyrrhizin, quercetin, rosmarinic acid, madecassic acid, chamazulene, bicalein and emodin. The composition of the present invention has all of excellent antioxidant, anti-inflammatory, wound-healing and moisturizing effects, thereby being widely used in medicine, cosmetic material or the like for the purpose of protecting the easily infectable, damaged and dried skin.

6 Claims, 1 Drawing Sheet

[Fig. 1]

COMPOSITIONS COMPRISING COMPOUNDS OF NATURAL ORIGIN FOR DAMAGED SKIN

TECHNICAL FIELD

The present invention relates to a skin-protecting composition for damaged skin, comprising glycyrrhizin, quercetin, rosmarinic acid, madecassic acid, chamazulene, bicalein and emodin.

BACKGROUND ART

Skin is the outermost organ of the body, and it has various functions and significantly affects our appearance and image. Total skin weight is about 3 to 5 kg of body weight, depending on a person's weight. Skin is made up of various cells and specific structure, and covers the outer surface of the body to function as a primary barrier against the external environment, including water conservation, temperature regulation, body protection from external stimuli such as UV, and protection from bacterial infection. Further, skin protects the body from physical or chemical injuries, infection caused by microorganisms (e.g., bacteria, fungi and parasites), UV damage, dryness or the like, and it also functions as sensory receptors in response to various external stimuli, and recognizes foreign antigens to generate immune cells.

Accordingly, skin may be easily damaged by external factors, whereby reactive oxygen species are abruptly produced, leading to stratum corneum damage. The stratum corneum damage is considered as a skin barrier impairment, which may proceed to a secondary infection by microorganisms. Subsequently, the damaged area may worsen to become a skin wound. Further, transdermal water loss through the damaged skin increases to cause dehydration. To prevent such event, abnormal sebum secretion occurs due to the abrupt secretion of sebum, resulting in excessive dryness or oiliness. Finally, such skin problems may be accompanied by itching, erythema, tissue damage or the like. Therefore, in order to minimize the tissue damage, a series of the above-described events should be suitably treated.

Recently, much of the focus has been placed on skin-protecting compositions comprising composite compounds of natural origin, for the purpose of preventing and improving skin damages, alleviating skin inflammation, or moisturizing skin. Examples of the natural extracts, which are used in the skin protecting compositions for the purpose of preventing and improving the skin damages, include animal/plant extracts, natural polymers such as collagen, cell activators such as amino acids and vitamins, and moisturizers such as glycerin and 1,3-butylene glycol. For example, Korean Patent No. 10-424726 discloses a skin-protecting cosmetic composition comprising vitamin C and phytosphingosine, and Korean Patent No. 10-364289 discloses a skin-protecting cosmetic composition comprising α-Hydroxy acid (AHA) and an epidermal growth factor (EGF) for alleviating skin irritation thereof.

However, there is a problem in that antioxidants, cell activators, or moisturizers used in the skin-protecting compositions should be separately used according to each purpose due to reactivity between each ingredients or incompatible properties, and formulation instability. Further, since approved ingredients that are allowed to be used in cosmetics, food, and medicine are different from each other, some ingredients used in medicine may not be used in cosmetics. For example, antibiotics are powerful materials to control microorganisms, but they can be used only in medical fields, not in cosmetics and food.

Accordingly, there is the need for materials that can be easily and safely used in medicine, cosmetics and food, while having antioxidant, anti-inflammatory, wound-healing and moisturizing effects.

Under such condition, the present inventors have conducted studies to develop composite materials that are safe upon application and easily used in various formulations, while having excellent antioxidant, anti-inflammatory, wound-healing and moisturizing effects, thereby completing the present invention.

DISCLOSURE OF INVENTION

Technical Problem

It is an object of the present invention to provide a skin-protecting composition comprising glycyrrhizin, quercetin, rosmarinic acid, madecassic acid, chamazulene, bicalein and emodin, which are compounds derived from plants being safe upon application and having excellent antioxidant, anti-inflammatory, wound-healing and moisturizing effects.

It is another object of the present invention to provide a pharmaceutical composition for treating or preventing dermatological diseases, comprising the skin-protecting composition as an active ingredient.

It is still another object of the present invention to provide a cosmetic material comprising the skin-protecting composition as an active ingredient.

BEST MODE FOR CARRYING OUT THE INVENTION

In one embodiment, the present invention relates to a skin-protecting composition comprising glycyrrhizin, quercetin, rosmarinic acid, madecassic acid, chamazulene, bicalein and emodin.

Glycyrrhizin, quercetin, rosmarinic acid, madecassic acid, chamazulene, bicalein and emodin contained in the skin-protecting composition of the present invention are compounds derived from plants, and they can be obtained by various known methods. For example, the compound can be obtained from plant extracts containing the compounds by fractionation, synthesized by chemical synthesis, or purchased from commercially available sources.

The glycyrrhizin of the present invention has been known as a compound that is a white or brown crystal extracted from licorice root and has an anti-inflammatory effect. The quercetin is present as its glycosides, and it has been known as a compound having an antioxidant effect and being commonly found in vegetables and fruits. The rosmarinic acid has been known as a compound that is contained in a rosemary plant extract and has an antioxidant effect. The madecas sic acid has been known as a compound that is contained in *Centella*

*asiatica* and has an antioxidant effect. The chamazulene has been known as a compound that is formed from matricarin in a german chamomile extract and has an anti-inflammatory effect. The bicalein has been known as a compound that is contained in extracts of *Scutellaria baicalensis* Georgi or the like and has soothing, antioxidant, and cell-protecting effects. The emodin has been known as a compound that is contained in *Polygonum cuspidatum* or wild yam and has an anticancer and anti-inflammatory effect.

The compounds contained in the composition of the present invention are compounds having excellent antioxidant, anti-inflammatory, wound-healing and moisturizing effects, among total compounds derived from natural plants (see Table 1). However, in each mixture of the compounds, any one effect of antioxidant, antiinflammatory, wound-healing and moisturizing effects was found to be better than that in each individual compound, and all of the effects were not found to increase. It was found that when the compounds were mixed in a specific ratio, all of the effects simultaneously increase (see Tables 2 and 3).

The composition ratio of glycyrrhizin:quercetin:rosmarinic acid:madecassic acid:chamazulene:bicalein:emodin is a weight ratio (g) of 1 to 5:2 to 10:0.5 to 2:0.5 to 2:1 to 5:1 to 5:1 to 5, and preferably a weight ratio (g) of 1 to 2:2 to 5:0.5 to 1:0.5 to 1:1 to 2:1 to 2:1 to 2.

Accordingly, the skin-protecting composition of the present invention, in which the compounds are mixed in a specific ratio, has all of significantly excellent antioxidant, anti-inflammatory, wound-healing and moisturizing effects, thereby being effectively used for protecting the damaged skin. Further, glycyrrhizin, quercetin, rosmarinic acid, madecassic acid, chamazulene, bicalein and emodin contained in the skin-protecting composition of the present invention are compounds derived from natural plants, and thus they have no cytotoxicity (Table 4), are safe for human skin (Table 5), and have no acute oral toxicity. Therefore, the compounds can be safely applied to humans, so as to be used in cosmetic materials and medicines.

The term "skin-protecting", as used herein, refers that skin damage by external stimulus or aging, inflammation by microorganisms, and dryness are prevented and the skin is improved.

A total weight of the compounds that are contained in the skin-protecting composition of the present invention is 0.001 to 50 wt %, preferably 0.001 to 30 wt %, and more preferably 0.001 to 20 wt %, based on the total weight of the composition.

The skin-protecting composition of the present invention may contain any known additional ingredient having antioxidant, anti-inflammatory, wound-healing and moisturizing effects, as long as it does not inhibit antioxidant, anti-inflammatory, wound-healing and moisturizing effects.

Examples of the additional ingredient may include a Forsythia Fructus extract, ascorbic acid, beta-carotene, dibutylated hydroxytoluene (BHT), and Dl-alpha-tocopherol having an antioxidant effect. Further, examples of the additional ingredient may include natural antiseptic materials such as a tea tree extract having an anti-inflammatory effect, and antibiotics such as tetracyclin, metronidazole, amoxicillin, and clarithromycin. Additionally, examples of the additional ingredient may include Polygonatum, Lily Bulb, Paeonia, Nelumbo semen, and Orpiment extracts having a moisturizing effect, and Saururus chinensis Baill, propwort, *Betula Platyphylla*, and *Juglans mandshurica* Maxim extracts having a wound-healing effect. The composition of the present invention may contain one or more of these additional ingredients at a content of 5 to 50 wt % within a range of effective content of the composition of the present invention.

In another embodiment, the present invention relates to a medicine and cosmetic material comprising the skin-protecting composition as an active ingredient.

The skin-protecting composition of the present invention has all of antioxidant, anti-inflammatory, wound-healing and moisturizing effects, thereby being widely used in medicine, cosmetics, and food for the purpose of restoring and improving damaged skin. In particular, it is possible to use the composition in medicine such as anti-inflammatory agents, antibiotics, and antifouling agents, in cosmetics or household products such as moisturizing products for atopy and psoriasis, other moisturizing products, anti-dandruff products having anti-microbial and anti-inflammatory effects, anti-microbial products for treating athlete's foot, osmidrosis, and acne, and anti-aging products having an antioxidant effect, but is not limited thereto.

In one specific embodiment, the present invention relates to a pharmaceutical composition for treating or preventing dermatological diseases, comprising the skin-protecting composition having all of the antioxidant, anti-inflammatory, wound-healing and moisturizing effects as an active ingredient.

Examples of the dermatological diseases include eczema, dermatitis, dermatitis medicamentosa, allergic dermatitis, toxic dermatitis, photoallergic dermatitis, atopic dermatitis and allergic asthma. In one specific embodiment, the pharmaceutical composition for treating or preventing dermatological diseases, which comprises the skin-protecting composition of the present invention as an active ingredient, exhibits the effect of significantly alleviating atopic dermatitis, as compared to the composition comprising purified water only (see FIG. 1). Therefore, the pharmaceutical composition comprising the skin-protecting composition of the present invention has an effect of treating or preventing dermatological diseases.

The pharmaceutical composition comprises the skin-protecting composition of about 1 to 50 wt %, and preferably about 1 to 20 wt %, based on the total weight of the composition.

According to the intended therapeutic purpose, the pharmaceutical composition may be formulated into pharmaceutical preparations common in the pharmaceutical field. For example, the formulations include tablets, capsules, powders, granules, suspensions, emulsions, syrups, emulsions in water, plasters, ointments, sprays, oils, gels, spirits, tinctures, baths, liniments, lotions, patches, pads and creams. Topical formulations are preferably used for direct application of the composition to a desired area of the external surface of the skin. Preferred topical formulations include ointments, lotions, sprays and gels. Topical formulations may be also contained in a support base or matrix directly applicable to a desired area of the skin. Examples of the support base include gauze or bandages. The pharmaceutical composition may be used in a colloidal or dried powder form in the formulations.

For ointment formulation, taking into consideration various factors including temperature of the skin surface, pH of the skin, transdermal water loss levels and total lipid levels of the epidermis, the present composition may be mixed with oligmous bases, which are exemplified by vaseline, liquid paraffin, paraffin, plastibase, silicon, lard, vegetable oils, waxes and purified lanolin, water-soluble bases, emulsion bases, suspension bases, and the like. The ointments may be supplemented with an antioxidant (e.g., tocopherol, BHA, BHT, NDGA), an antiseptic (e.g., phenolic compounds, chlorobutanol, benzylalcohol, parabens, benzoic acid), a humectant (e.g., glycerin, propylene glycol, sorbitol), a solution adjuvant (e.g., ethanol, propylene glycol), a softening adjuvant (e.g., liquid paraffin, glycerin, propylene glycol, surfactants), and other additives.

For lotion formulation, the present composition may be formulated into various lotion forms including solutions, suspensions and emulsions. For lotions to be applied to the skin, the present composition may be formulated into lotions, for example, with a viscosity of 200 cps to 500 cps, and may be preferably supplemented with a humectant such as glycerin or propylene glycol to give a soft feeling upon application to the skin.

For spray formulation, the additives may be mixed with a propellant to disperse a water-dispersed concentrate or humidified powder.

For patch formulation, a permeation stimulator may be used to increase the permeation of compounds through the skin.

The pharmaceutical composition of the present invention may be administered by various routes, for example, oral, parenteral, or topical administration, preferably parenteral and topical administrations, and more preferably topical administration. The topical administration includes transcutaneous injection bringing about systemic effects. Preparations for topical administration may include an excipient (e.g., lactose, starch, cellulose, lactose, polyethylene glycol), a lubricant (e.g., magnesium stearate, stearic acid, glyceryl behenate, talc), and a preservative (e.g., benzalkonium chloride).

The present composition may be administered in a pharmaceutically effective amount. The term "pharmaceutically effective amount", as used herein, refers to an amount sufficient for treatment or prevention of diseases, which is commensurate with a reasonable benefit/risk ratio applicable for medical treatment or prevention. An effective dosage of the present composition may be determined depending on the patient's diseases and severity of the diseases; drug activity; the patient's age, body weight, health state and gender; the patient's drug sensitivity; administration time, administration routes and excretion rates of a used extract; duration of treatment; drugs used in combination with or simultaneously used with a used extract; and other factors known in medical fields. Typically, the present composition may be administered at a daily dosage of about 0.1 to 1000 mg/kg, preferably 10 to 100 mg/kg one time or several times.

The skin-protecting composition and additional ingredients contained in the pharmaceutical composition of the present invention have substantially no toxicity and adverse side-effects, thereby being safely used.

In another specific embodiment, the present invention relates to a cosmetic material having antioxidant, anti-inflammatory, wound-healing and moisturizing effects, comprising the skin-protecting composition of the present invention as an effective ingredient.

The skin-protecting composition contained in the cosmetic material of the present invention is 0.01 to 20 wt %, preferably 0.01 to 10 wt %, and most preferably 0.1 to 3.0 wt %, based on the total weight of the cosmetic material.

The ingredients contained in the cosmetic material of the present invention are effective ingredients, including commonly used ingredients in the cosmetic material, in addition to the composition. Such ingredients include, for example, conventional auxiliary agents such as a thickening agent, a stabilizer, a solubilizing agent, a vitamin, a pigment, and a flavor, and a carrier.

The cosmetic material of the present invention can be prepared as any formulation commonly prepared in the art. The cosmetic material can be formulated as, for example, a solution, a suspension, an emulsion, a paste, a gel, a cream, a lotion, a powder, a soap, a surfactant-containing cleanser, an oil, a powdered foundation, an emulsion foundation, a wax foundation, a spray, or the like, but not limited thereto. More specifically, the cosmetic material can be prepared as a formulation such as a softening toner, a nutrient toner, a nutrient cream, a massage cream, an essence, an eye cream, a cleansing cream, a cleansing foam, a cleansing water, a pack, a spray, and a powder.

If the formulation of the cosmetic material of the present invention is a paste, a cream or a gel, an animal oil, a vegetable oil, a wax, paraffin, a starch, traganth, a cellulose derivative, a polyethylene glycol, silicone, bentonite, silica, talc, zinc oxide, or the like can be used as the carrier ingredient.

If the formulation of the cosmetic material of the present invention is a paste, a cream or a gel, lactose, talc, silica, aluminum hydroxide, calcium silicate, or polyamide powders can be used as the carrier ingredient, and in particular, if the formulation is a spray, a propellent such as chlorofluorohydrocarbon, propane/butane or dimethyl ether can be used.

If the formulation of the cosmetic material of the present invention is a solution or an emulsion, a solvent, a solubilizing agent or an emulsifier can be used as the carrier ingredient, and examples thereof include water, ethanol, isopropanol, ethyl carbonate, ethyl acetate, benzyl alcohol, benzyl benzoate, propylene glycol, 1,3-butylglycol oil, glycerol aliphatic esters, polyethylene glycol or sorbitan fatty acid esters.

If the formulation of the cosmetic material of the present invention is a suspension, a liquid diluent such as water, ethanol and propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, traganth, or the like can be used as the carrier ingredient.

If the formulation of the cosmetic material of the present invention is a surfactant-containing cleanser, aliphatic alcohol sulfate, aliphatic alcohol ether sulfate, sulphosuccinic acid monoester, isethionate, imidazolinium derivative, methyltaurate, sarcosinate, fatty acid amide ether sulfate, alkylamidobetain, aliphatic alcohol, fatty acid glyceride, fatty acid diethanolamide, vegetable oils, a lanolin derivative or ethoxylated glycerol fatty acid ester, or the like can be used as the carrier ingredient.

The composition contained in the cosmetic material of the present invention has substantially no toxicity and adverse side-effects, thereby being safely used in the cosmetic material.

MODE FOR THE INVENTION

Hereinbelow, the present invention will be described in more detail with reference to Examples. Examples are provided only for the purpose of illustrating the present invention, and accordingly it is not intended that the present invention is limited thereto.

Example 1

Selection of Compound Having Four Efficacies

Compounds that have been known to have an antioxidant, anti-inflammatory, wound-healing or moisturizing effect were selected from the compounds derived from natural plants that have been used in medicine, food, and cosmetics using Pubmed (www.ncbi.nlm.nih.gov). The selected compounds were tested for their antioxidant, anti-inflammatory, wound-healing and moisturizing efficacies.

Determination of Antioxidant Activity

In order to confirm the antioxidant activity of the compounds, a DPPH method was employed. DPPH (1,1-diphenyl-2-picrylhydrazyl) is a chromogenic radical and thus, can be used to directly confirm the radical scavenging activity of the samples. The samples were dissolved in 4 ml of distilled water or solvent (methanol) and then, mixed well with 1 ml of 100 µM DPPH. Subsequently, the samples were incubated at room temperature for 30 minutes. The absorbance of the remaining DPPH was measured at 517 nm. As a blank of the present experiment, distilled water or solvent was used, and as a control, an experimental group composed only of DPPH in distilled water or solvent without the sample was used. Further, vitamin C was used as a positive control. As a result, the antioxidant activity was expressed as percentages of the absorbance of each hydrolysate relative to the absorbance of control, as calculated by the following equation 1.

$$RSA(\%) = \frac{Abs \cdot of\ hydroxylate}{Abs \cdot of\ Control} \times 100 \quad \text{(Experimental Equation 1)}$$

(RSA: Radical Scavenging Activity)

Determination of Anti-Inflammatory Effect

The anti-inflammatory effect was determined by the inhibition test of NF-kB luciferase activity. Human fibroblasts and mouse fibroblasts, NIH3T3 were transfected with NF-kB reporter DNA using SuperFect to induce transformation. At 24 hrs after transformation, the samples were treated with TNF-alpha (10 ng/ml). After 16 hrs, the cells were collected, and luminescence measurements were made at 450 nm using a Luminometer (Berthold, Germany).

Determination of wound-healing effect

The wound-healing effect was determined by a cell migration assay. Human keratinocytes were confluently cultured in keratinocyte-SFM media and then, treated with ug/ml mitomycin C (Sigma Chemical) to inhibit cell growth for the measurement of cell migration. The confluent cell monolayer was scratched using a yellow pipette tip to create a cell-free region and then, the cell debris was washed with PBS. After the treatment, the samples were cultured in keratinocyte-SFM media for 48 hrs to observe the effect on cell migration (Cecile A et. al., Molecular Biology of the Cell, 2002; 13: 3845-3858).

Determination of Moisturizing Effect

The transepidermal water loss was measured using a Tewameter TM210 (Germany). The measurement was performed twice, before the treatment and at 2 weeks after the treatment, and the results were statistically compared. The measurement was performed in a temperature/humidity controlled room (no air flow, no light, at a temperature of 22° C. and relative humidity of 40%). The measurement was performed in the abdomen of thirty subjects.

Results

Of the results for total 50 kinds of compounds, the results for 30 kinds of compounds, which exhibit two or more effects, are summarized in Table 1. In order to confirm that the selected compounds had all of four efficacies, the tests were performed. Then, the compounds having all of antioxidant, anti-inflammatory, wound-healing and moisturizing effects at a predetermined level were selected.

TABLE 1

Result of physiological/biochemical analysis of compound of natural Origin

| Compound | Antioxidant effect | Anti-inflammatory effect | Wound-healing effect | Moisturizing effect | Selection |
|---|---|---|---|---|---|
| Glycyrrhizin | ++ | ++ | ++ | ++ | O |
| Quercetin | ++ | ++ | ++ | ++ | O |
| Coenzyme Q10 | + | − | + | + | |
| Linolenic acid | + | ++ | ++ | ++ | |
| Rutin | + | + | + | + | |
| Rosmarinic acid | ++ | ++ | ++ | ++ | O |
| Garlic acid | + | + | + | − | |
| Magnolol | + | + | + | − | |
| Honokiol | + | + | ++ | − | |
| Madecassic acid | ++ | ++ | ++ | ++ | O |
| Furaneol | + | + | + | + | |
| Pinosylvin | + | + | ++ | − | |
| Ascorbic acid | + | + | ++ | − | |
| Geraniol | + | ++ | + | − | |
| alpha-Tocopherol | + | + | ++ | | |
| Diosgenin | − | + | ++ | + | |
| Oleic acid | + | + | + | + | |
| Elaidic acid | + | + | + | − | |
| Indole-3-carbinol | + | + | + | − | |
| Hydroxytyrosol | + | + | + | + | |
| Ginsenoside Rb1 | − | + | + | + | |
| Coumarin | + | ++ | + | − | |
| Phytic acid | + | + | ++ | − | |
| Caffeic acid | + | + | + | + | |
| alpha-lipoic acid | + | + | ++ | − | |
| Chamazulene | ++ | ++ | ++ | ++ | O |
| Retinol | + | + | + | − | |
| Emodin | ++ | ++ | ++ | ++ | O |
| Baicalein | ++ | ++ | ++ | ++ | O |

−: No effect, +: Weak effect, ++: Moderate effect, +++: Strong effect, ++++: Very strong effect Example 2

Composition Ratio of Composite Compound for Skin-Protecting Composition

Glycyrrhizin (Sigma), quercetin (Sigma), rosmarinic acid (A.G. Scientific Inc.), madecassic acid (Sigma), chamazulene (Sigma), bicalein (Sigma), and emodin (Sigma) obtained in Example 1 were mixed in various ratios to prepare composite compounds. A total concentration of the composite compound was fixed at 7 ug/ml, based on an effective concentration of each compound, 1 ug/ml. Based on this, composite compounds were prepared according to 90 kinds of composition ratios, which are shown in the following Table 2.

TABLE 2

Concentration ratio of compounds for preparation of composite compound (ug/ml)

| Compound No. | Glycyrrhizin | Quercetin | Rosemarinic acid | Nadecassic acid | Chamazulene | Emodin | Bicalein |
|---|---|---|---|---|---|---|---|
| 1 | 1 | 1 | 1 | 1 | 1 | 1 | 1 |
| 2 | 1 | 1.5 | 0.5 | 1 | 1 | 1 | 1 |
| 3 | 1 | 1 | 1.5 | 0.5 | 1 | 1 | 1 |
| 4 | 1 | 1 | 1 | 1.5 | 0.5 | 1 | 1 |

TABLE 2-continued

Concentration ratio of compounds for preparation of composite compound (ug/ml)

| Compound No. | Glycyr-rhizin | Quer-cetin | Rose-marinic acid | Nade-cassic acid | Chama-zulene | Emo-din | Bi-calein |
|---|---|---|---|---|---|---|---|
| 5 | 1 | 1 | 1 | 1 | 1.5 | 0.5 | 1 |
| 6 | 1 | 1 | 1 | 1 | 1 | 1.5 | 0.5 |
| 7 | 0.5 | 1 | 1 | 1 | 1 | 1 | 1.5 |
| 8 | 1 | 1.5 | 1 | 0.5 | 1 | 1 | 1 |
| 9 | 1 | 1.5 | 1 | 1 | 0.5 | 1 | 1 |
| 10 | 1 | 1.5 | 1 | 1 | 1 | 0.5 | 1 |
| 11 | 1 | 1.5 | 1 | 1 | 1 | 1 | 0.5 |
| 12 | 1 | 1 | 1.5 | 1 | 0.5 | 1 | 1 |
| 13 | 1 | 1 | 1.5 | 1 | 1 | 0.5 | 1 |
| 14 | 1 | 1 | 1.5 | 1 | 1 | 1 | 0.5 |
| 15 | 1 | 1 | 1 | 1.5 | 1 | 0.5 | 1 |
| 16 | 1 | 1 | 1 | 1.5 | 1 | 1 | 0.5 |
| 17 | 1 | 1 | 1 | 1 | 1.5 | 1 | 0.5 |
| 18 | 0.5 | 1 | 1 | 1 | 1 | 1.5 | 1 |
| 19 | 1 | 0.5 | 1 | 1 | 1 | 1 | 1.5 |
| 20 | 1 | 1 | 0.5 | 1 | 1 | 1 | 1.5 |
| 21 | 1 | 1 | 1 | 0.5 | 1 | 1 | 1.5 |
| 22 | 1 | 1 | 1 | 1 | 0.5 | 1 | 1.5 |
| 23 | 1 | 1 | 1 | 1 | 1 | 0.5 | 1.5 |
| 24 | 1 | 2 | 0.5 | 0.5 | 1 | 1 | 1 |
| 25 | 1 | 1 | 2 | 0.5 | 0.5 | 1 | 1 |
| 26 | 1 | 1 | 1 | 2 | 0.5 | 0.5 | 1 |
| 27 | 1 | 1 | 1 | 1 | 2 | 0.5 | 0.5 |
| 28 | 0.5 | 1 | 1 | 1 | 1 | 2 | 0.5 |
| 29 | 0.5 | 0.5 | 1 | 1 | 1 | 1 | 2 |
| 30 | 2 | 0.5 | 0.5 | 1 | 1 | 1 | 1 |
| 27 | 1 | 2 | 0.5 | 1 | 0.5 | 1 | 1 |
| 28 | 1 | 2 | 0.5 | 1 | 1 | 0.5 | 1 |
| 29 | 1 | 2 | 1 | 0.5 | 0.5 | 1 | 1 |
| 30 | 1 | 1 | 2 | 0.5 | 1 | 0.5 | 1 |
| 31 | 1 | 1 | 2 | 0.5 | 1 | 1 | 0.5 |
| 31 | 0.5 | 1 | 2 | 0.5 | 1 | 1 | 1 |
| 33 | 1 | 0.5 | 2 | 0.5 | 1 | 1 | 1 |
| 34 | 1 | 2.5 | 0.5 | 0.5 | 0.5 | 1 | 1 |
| 35 | 1 | 1 | 2.5 | 0.5 | 0.5 | 0.5 | 1 |
| 36 | 1 | 1 | 1 | 2.5 | 0.5 | 0.5 | 0.5 |
| 37 | 0.5 | 1 | 1 | 1 | 2.5 | 0.5 | 0.5 |
| 38 | 0.5 | 0.5 | 1 | 1 | 1 | 2.5 | 0.5 |
| 39 | 0.5 | 0.5 | 0.5 | 1 | 1 | 1 | 2.5 |
| 40 | 2.5 | 0.5 | 0.5 | 0.5 | 1 | 1 | 1 |
| 41 | 1 | 2.5 | 0.5 | 0.5 | 1 | 0.5 | 1 |
| 42 | 1 | 2.5 | 0.5 | 0.5 | 1 | 1 | 0.5 |
| 43 | 0.5 | 2.5 | 0.5 | 0.5 | 1 | 1 | 1 |
| 44 | 1 | 2.5 | 0.5 | 1 | 0.5 | 0.5 | 1 |
| 45 | 1 | 2.5 | 0.5 | 1 | 1 | 0.5 | 0.5 |
| 46 | 0.5 | 2.5 | 0.5 | 1 | 1 | 1 | 0.5 |
| 47 | 1 | 0.5 | 1.5 | 1 | 1 | 1 | 1 |
| 48 | 1 | 1 | 0.5 | 1.5 | 1 | 1 | 1 |
| 49 | 1 | 1 | 1 | 0.5 | 1.5 | 1 | 1 |
| 50 | 1 | 1 | 1 | 1 | 0.5 | 1.5 | 1 |
| 51 | 1 | 1 | 1 | 1 | 1 | 0.5 | 1.5 |
| 52 | 1.5 | 1 | 1 | 1 | 1 | 1 | 0.5 |
| 53 | 0.5 | 1.5 | 1 | 1 | 1 | 1 | 1 |
| 54 | 1 | 0.5 | 1 | 1.5 | 1 | 1 | 1 |
| 55 | 1 | 0.5 | 1 | 1 | 1.5 | 1 | 1 |
| 56 | 1 | 0.5 | 1 | 1 | 1 | 1.5 | 1 |
| 57 | 1 | 0.5 | 1 | 1 | 1 | 1 | 1.5 |
| 58 | 1.5 | 0.5 | 1 | 1 | 1 | 1 | 1 |
| 59 | 1 | 1 | 0.5 | 1 | 1.5 | 1 | 1 |
| 60 | 1 | 1 | 0.5 | 1 | 1 | 1.5 | 1 |
| 61 | 1 | 1 | 0.5 | 1 | 1 | 1 | 1.5 |
| 62 | 1.5 | 1 | 0.5 | 1 | 1 | 1 | 1 |
| 63 | 1 | 1.5 | 0.5 | 1 | 1 | 1 | 1 |
| 64 | 1 | 1 | 1 | 0.5 | 1 | 1.5 | 1 |
| 65 | 1 | 1 | 1 | 0.5 | 1 | 1 | 1.5 |
| 66 | 1.5 | 1 | 1 | 0.5 | 1 | 1 | 1 |
| 67 | 1 | 1.5 | 1 | 0.5 | 1 | 1 | 1 |
| 68 | 1 | 1 | 1.5 | 0.5 | 1 | 1 | 1 |
| 69 | 1 | 1 | 1 | 1 | 0.5 | 1 | 1.5 |
| 70 | 1.5 | 1 | 1 | 1 | 0.5 | 1 | 1 |
| 71 | 1 | 1.5 | 1 | 1 | 0.5 | 1 | 1 |
| 72 | 1 | 1 | 1.5 | 1 | 0.5 | 1 | 1 |
| 73 | 1 | 1 | 1 | 1.5 | 0.5 | 1 | 1 |
| 74 | 1 | 2.5 | 0.5 | 0.5 | 0.5 | 1 | 1 |
| 75 | 1 | 1 | 2.5 | 0.5 | 0.5 | 0.5 | 1 |
| 76 | 1 | 1 | 1 | 2.5 | 0.5 | 0.5 | 0.5 |
| 77 | 0.5 | 1 | 1 | 1 | 2.5 | 0.5 | 0.5 |
| 78 | 0.5 | 0.5 | 1 | 1 | 1 | 2.5 | 0.5 |
| 79 | 0.5 | 0.5 | 0.5 | 1 | 1 | 1 | 2.5 |
| 80 | 2.5 | 0.5 | 0.5 | 0.5 | 1 | 1 | 1 |
| 81 | 1 | 2.5 | 0.5 | 0.5 | 1 | 0.5 | 1 |
| 82 | 1 | 2.5 | 0.5 | 0.5 | 1 | 1 | 0.5 |
| 83 | 0.5 | 2.5 | 0.5 | 0.5 | 1 | 1 | 1 |
| 84 | 1 | 2.5 | 0.5 | 1 | 0.5 | 0.5 | 1 |
| 85 | 1 | 2.5 | 0.5 | 1 | 1 | 0.5 | 0.5 |
| 86 | 0.5 | 2.5 | 0.5 | 1 | 1 | 1 | 0.5 |
| 87 | 1 | 2.5 | 1 | 0.5 | 0.5 | 0.5 | 1 |
| 88 | 1 | 2.5 | 1 | 1 | 0.5 | 0.5 | 0.5 |
| 89 | 0.5 | 2.5 | 1 | 1 | 1 | 0.5 | 0.5 |
| 90 | 1 | 1 | 2.5 | 0.5 | 0.5 | 1 | 0.5 |
| 91 | 7 | 0 | 0 | 0 | 0 | 0 | 0 |
| 92 | 0 | 7 | 0 | 0 | 0 | 0 | 0 |
| 93 | 0 | 0 | 7 | 0 | 0 | 0 | 0 |
| 94 | 0 | 0 | 0 | 7 | 0 | 0 | 0 |
| 95 | 0 | 0 | 0 | 0 | 7 | 0 | 0 |
| 96 | 0 | 0 | 0 | 0 | 0 | 7 | 0 |
| 97 | 0 | 0 | 0 | 0 | 0 | 0 | 7 |

Example 3

Composition Ratio of Composite Compound for Skin-Protecting Composition

Each composite compound of Example 2 was subjected to the determination tests according to Example 1 to examine the antioxidant, anti-inflammatory, wound-healing and moisturizing effects. The results are shown in Table 3.

TABLE 3

Result of physiological/biochemical analysis

| Composite Compound No. | Anti-oxidant effect | Anti-infalammatory effect | Wound-healing effect | Moisturizing effect |
|---|---|---|---|---|
| 1 | +++ | ++ | +++ | ++ |
| 2 | +++ | ++ | +++ | ++ |
| 3 | ++ | ++ | +++ | ++ |
| 4 | ++ | ++ | ++ | ++ |
| 5 | ++ | +++ | +++ | +++ |
| 6 | ++ | ++ | +++ | ++ |
| 7 | ++ | ++ | ++ | + |
| 8 | ++ | ++ | +++ | + |
| 9 | ++ | ++ | ++ | ++ |
| 10 | ++ | ++ | +++ | ++ |
| 11 | ++ | ++ | ++ | ++ |
| 12 | ++ | ++ | ++ | ++ |
| 13 | ++ | ++ | ++ | ++ |
| 14 | ++ | ++ | ++ | ++ |
| 15 | ++ | ++ | +++ | ++ |
| 16 | ++ | ++ | +++ | ++ |
| 17 | ++ | ++ | ++ | ++ |
| 18 | ++ | ++ | +++ | +++ |
| 19 | ++ | ++ | +++ | ++ |
| 20 | ++ | ++ | ++ | ++ |
| 21 | ++ | ++ | +++ | ++ |
| 22 | ++ | ++ | ++ | ++ |
| 23 | +++ | ++ | ++ | ++ |
| 24 | ++++ | ++++ | ++++ | +++ |
| 25 | ++ | +++ | +++ | +++ |

TABLE 3-continued

Result of physiological/biochemical analysis

| Composite Compound No. | Anti-oxidant effect | Anti-inflammatory effect | Wound-healing effect | Moisturizing effect |
|---|---|---|---|---|
| 26 | ++ | ++ | +++ | ++ |
| 27 | +++ | +++ | +++ | ++ |
| 28 | ++ | +++ | +++ | ++ |
| 29 | +++ | ++ | +++ | ++ |
| 30 | +++ | ++ | ++ | ++ |
| 31 | ++ | +++ | +++ | ++ |
| 32 | ++ | +++ | ++ | ++ |
| 33 | ++ | +++ | ++ | ++ |
| 34 | ++ | ++ | ++ | +++ |
| 35 | ++ | ++ | +++ | ++ |
| 36 | +++ | ++ | ++ | ++ |
| 37 | ++ | +++ | ++ | ++ |
| 38 | ++ | ++ | +++ | ++ |
| 39 | +++ | +++ | ++ | ++ |
| 40 | +++ | ++ | ++ | ++ |
| 41 | ++ | ++ | +++ | ++ |
| 42 | ++ | +++ | +++ | ++ |
| 43 | ++ | ++ | ++ | +++ |
| 44 | ++ | +++ | ++ | ++ |
| 45 | ++ | ++ | +++ | ++ |
| 46 | ++ | ++ | ++ | ++ |
| 47 | +++ | ++ | +++ | ++ |
| 48 | +++ | ++ | ++ | ++ |
| 49 | ++ | +++ | ++ | ++ |
| 50 | +++ | +++ | ++ | ++ |
| 51 | ++ | +++ | ++ | ++ |
| 52 | ++ | +++ | +++ | ++ |
| 53 | +++ | ++ | ++ | ++ |
| 54 | ++ | +++ | ++ | ++ |
| 55 | +++ | ++ | +++ | ++ |
| 56 | ++ | +++ | +++ | ++ |
| 57 | +++ | +++ | +++ | ++ |
| 58 | ++ | ++ | +++ | ++ |
| 59 | ++ | +++ | ++ | ++ |
| 60 | ++ | +++ | ++ | ++ |
| 61 | ++ | +++ | +++ | ++ |
| 62 | ++ | ++ | ++ | ++ |
| 63 | ++ | +++ | +++ | ++ |
| 64 | +++ | ++ | ++ | ++ |
| 65 | +++ | +++ | +++ | ++ |
| 66 | ++ | ++ | ++ | +++ |
| 67 | ++ | ++ | +++ | ++ |
| 68 | ++ | +++ | ++ | ++ |
| 69 | +++ | +++ | ++ | ++ |
| 70 | ++ | ++ | +++ | ++ |
| 71 | +++ | +++ | ++ | +++ |
| 72 | ++ | +++ | ++ | ++ |
| 73 | ++ | ++ | ++ | ++ |
| 74 | +++ | +++ | ++ | ++ |
| 75 | +++ | +++ | ++ | ++ |
| 76 | ++ | +++ | ++ | ++ |
| 77 | +++ | ++ | +++ | ++ |
| 78 | ++ | +++ | ++ | +++ |
| 79 | +++ | ++ | +++ | ++ |
| 80 | ++ | ++ | +++ | ++ |
| 81 | +++ | +++ | ++ | ++ |
| 82 | ++ | ++ | +++ | ++ |
| 83 | ++ | ++ | ++ | ++ |
| 84 | ++ | ++ | +++ | +++ |
| 85 | +++ | +++ | ++ | +++ |
| 86 | ++ | +++ | +++ | ++ |
| 87 | +++ | ++ | +++ | ++ |
| 88 | ++ | ++ | ++ | +++ |
| 89 | +++ | +++ | +++ | ++ |
| 90 | ++ | +++ | +++ | ++ |
| 91 | ++ | ++ | ++ | ++ |
| 92 | ++ | ++ | ++ | ++ |
| 93 | ++ | ++ | ++ | ++ |
| 94 | ++ | ++ | ++ | ++ |
| 95 | ++ | ++ | ++ | ++ |
| 96 | ++ | ++ | ++ | ++ |
| 97 | ++ | ++ | ++ | ++ |

−: No effect, +: Weak effect, ++: Moderate effect, +++: Strong effect, ++++: Very strong effect As shown in Table 3, the composite compounds substantially exhibited higher effects than the individual compound. However, no specific correlation between composition ratio and efficacy was found. Of the 90 kinds of composition ratios, the most optimal composition ratio was found to be NO. 24 (Table 3). The composition ratio of NO. 24 is 1:2:0.5:0.5:1:1:1 (glycyrrhizin:quercetin:rosmarinic acid:madecassic acid:chamazulene:emodin:bicalein), and the composite compound having the ratio was designated as BASAM in the present invention. From the result, it can be seen that BASAM, which is the composite compound of the present invention prepared in a specific composition ratio, exhibits the most ideal effects (Table 3).

Example 4

Cytotoxicity Test of Composite Compound

In order to examine the safety of the composite compound (BASAM) having the most excellent efficacies, which had been found in Example 3, a cytotoxicity test (MTT) was performed using a human keratinocyte cell line, HaCaT in the present Example. The HaCaT cells were treated with the sample and then, cultured in serum free media. The cells were subjected to an MTT assay to test cytotoxic effects. MTT (3-(4,5-dimethylthiazol-2-yl)2,5-diphenyltetrazolium bromide) is a pale yellow substrate that is cleaved by mitochondrial dehydrogenase enzymes in living cells to yield a dark blue formazan product, but not by dead cells. Therefore, the amount of produced formazan is used for the measurement of cell viability. The results are shown in Table 4.

TABLE 4

Cytotoxicity of composite compound (BASAM)

| Conc. of composite compound (BASAM) (ug/ml) | | | | | | | | |
|---|---|---|---|---|---|---|---|---|
| | 0 | 10 | 20 | 50 | 100 | 500 | 1000 | 2000 | 3000 |
| Cell viability | 100 | 101 | 99.9 | 99.7 | 99.7 | 99.2 | 99.2 | 87.2 | 81.5 |

As shown in Table 4, no cytotoxicity was observed by 15 mg/ml or less of the composite compound, BASAM in HaCaT cells. However, the cytotoxicity was slightly observed at a concentration of 20/ml or more.

Example 5

Safety Test of Composite Compound for Human Skin

The composite compound was found to show no cytotoxicity in the cytotoxicity test of Example 5. Subsequently, in order to examine the safety of the composite compound on human skin, a skin safety test was performed. A cumulative irritation test method was employed.

Squalane, which has been known to have no irritation to human skin, was used as a base to prepare formulations. Each formulation contained 1 mg/ml, 10 mg/ml, 20 mg/ml and 30 mg/ml of BASAM. The composition of the present invention (BASAM) was added to squalane, and mixed using a homogenizer at 3000 rpm for 5 minutes at room temperature to prepare the formulations. In order to confirm whether the composite compound (BASAM) causes skin irritation, a cumulative patch test was performed using the prepared samples, in which the samples were prepared in the form of patches and applied every other day to the forearms of 30 healthy adults, and left for 24 hours, and this was repeated so that each subject was treated with 9 fresh patches in total.

The patch test was performed using a Finn chamber (Epitest Ltd, Finland). The topical agents were loaded dropwise in an amount of 15☐ per patch on the chamber. At every round of the patch application, the response of the skin was scored using the following Experimental Equation 2, and the results are shown in the following Table 5. In regard to the response degree, 1 point was provided for ±, 2 points for +, 4 points for ++. When the average response degree was less than 3, the composition was determined to be safe for the skin.

Average response degree=[Response index×Response degree/Total number of subjects×Highest score (4 points)]÷Times of examination (9 rounds)    (Experimental Equation 2)

Example 6

Acute Oral Toxicity Assay

In order to examine whether the composite compound of the present invention (BASAM) is safe, an acute oral toxicity assay was conducted thereon (Korea Testing & Research Institute). 20 SPF SD rats, all 5~6 weeks old, were subjected to the acute oral toxicity assay under the following conditions.

Temperature and humidity: 22° C.+/−2° C., RH 50+/−10%
Light-dark cycle: fluorescent lamp (Turn-On at 8 A.M., Turn-Off at 8 P.M.)
Illuminance: 200~300 Lux
Allowed to freely approach UV-treated water
Dilutions of the test substance in sterile distilled water were administered while the same volume of sterile distilled water was used as a control.

On the day of administration, the rats were observed for their general condition every hour for 4 hrs after the administration. From 1 to 14 days after the administration, the rats were carefully observed once a day for general state, toxicity symptoms, motility, appearance, change in the autonomic nervous system, and death. Autopsies were also performed to determine the toxicity of the composite composition. The composite composition of the present invention was determined to have an $LD_{50}$ of 3000 mg/kg B.W. and no toxicity.

TABLE 5

| Test Material | Nos. of Subjects in response | | | | | | | | | Avg. Response Degree |
|---|---|---|---|---|---|---|---|---|---|---|
| | Week 1 | | | Week 2 | | | Week 3 | | | |
| | $1^{st}$ ±+ ++ | $2^{nd}$ ±+ ++ | $3^{rd}$ ±−+ | $4^{th}$ ±−+ | $5^{th}$ ±−+ | $6^{th}$ ±−+ | $7^{th}$ ±−+ | $8^{th}$ ±−+ | $9^{th}$ ±−+ | |
| Squalene (Control) | 2− − | − − − | − − − | − − − | − − − | − − − | − − − | − − − | − − − | 0.18 |
| Composite compound (BASAM) (1 mg/ml, Group 1) | 2− − | 0− − | − − − | − − − | − − − | − − − | − − − | − − − | − − − | 0.18 |
| Composite compound (BASAM) (10 mg/ml, Group 2) | 2− − | 0− − | − − − | − − − | − − − | − − − | − − − | − − − | − − − | 0.18 |
| Composite compound (BASAM) (20 mg/ml, Group 3) | 2− − | 0− − | − − − | − − − | − − − | − − − | − − − | − − − | − − − | 0.18 |
| Composite compound (BASAM) (30 mg/ml, Group 4) | 2− − | 0− − | − − − | − − − | − − − | − − − | − − − | − − − | − − − | 0.18 |
| No. of subjects | 30 | 30 | 30 | 30 | 30 | 30 | 30 | 30 | 30 | |

As shown in Table 5, the subjects corresponding to ±, + and ++ in Test Group 1 numbered 2, 0 and 0, respectively, while the others showed no response. According to Experimental Equation 2, all of the average response degrees of Test Groups 1 to 4 were calculated to be 0.18, which all are less than 3, demonstrating that the composite compound of the present invention (BASAM) causes no noticeable cumulative irritation and is safe for human skin.

Example 7

Preparation of Skin-Improving Cosmetic Composition Containing Composite Compound Nutrient Cream Containing Composite Compound (BASAM)

Preparation Example of a nutrient cream containing the composite compound (BASAM) is the same as in the following Table 6. Purified water (aqueous phase), tri-ethanolamine, propylene glycol were dissolved by heating at 70° C. Thereto was added a solution (oil phase), in which fatty acids, oily ingredient, emulsifier, and preservative were dissolved by heating at 70° C., to perform emulsification. After the emulsification, the solution was cooled to 45° C. Then, the composite compound (BASAM) and perfume were added thereto, and dispersed to be cooled to 30° C.

TABLE 6

Ingredients and content of nutrient cream containing composite compound (BASAM)

| Ingredients | Content (wt %) |
|---|---|
| Composite compound (BASAM) | 0.1%, 1%, 3% or 5% |
| Jojoba oil | 4.0 |
| Liquid paraffin | 5.0 |
| Cetearyl alcohol | 1.5 |
| Polyglyceryl-3 methyl glucose distearate | 1.5 |
| Glyceryl stearate | 0.5 |
| Squalane | 2.0 |
| Propylene glycol | 2.0 |
| Glycerin | 6.0 |
| Triethanolamine | 0.2 |
| Carboxy vinylpolymer | 0.2 |
| Tocopheryl acetate | 0.3 |
| Preservative, perfume | Trace amount |
| Purified water | Residual amount |
| Total | 100 |

Comparative Preparation Example

Cream Containing Purified Water

Cream containing purified water was prepared in the same manner as in Preparation Example, except that purified water was used instead of the composite compound. The ingredients are as follows.

TABLE 7

Ingredients and content of nutrient cream containing no composite compound (BASAM)

| Ingredients | Content (wt %) |
|---|---|
| Jojoba oil | 4.0 |
| Liquid paraffin | 5.0 |
| Cetearyl alcohol | 1.5 |
| Polyglyceryl-3 methyl glucose distearate | 1.5 |
| Glyceryl stearate | 0.5 |
| Squalane | 2.0 |
| Propylene glycol | 2.0 |
| Glycerin | 6.0 |
| Triethanolamine | 0.2 |
| Carboxy vinylpolymer | 0.2 |
| Tocopheryl acetate | 0.3 |
| Preservative, perfume | Trace amount |
| Purified water | Residual amount |
| Total | 100 |

Example 8

Test for Skin-Improving Effect

The skin was stimulated with SDS (0.01%) to cause damage to skin tissue. Then, the nutrient cream containing the composite compound of the present invention was applied to the forearm through patches to observe whether the skin tissue was improved. 30 healthy adults were subjected to this test.

The patch test was performed using a Finn chamber (Epitest Ltd, Finland). The topical agents were loaded dropwise in an amount of 15□ per patch on the chamber. Every round of the patch application, the response of the skin was scored using the following Experimental Equation 3, and the results are shown in the following Table 8.

Average response degree=[Response index×Response degree/Total number of subjects×Highest score (4 points)×100]/Times of examination (9 rounds)   (Experimental Equation 3)

In regard to the response degree, 1 point was provided for ±, 2 points for +, 4 points for ++.

TABLE 8

| | Response Degree | | | Avg. |
|---|---|---|---|---|
| Test Material | Week 1 | Week 2 | Week 3 | Response Degree |
| Squalene (Control) | 0.15 | 0.15 | 0.12 | 0.14 |
| SDS (0.01%) | 4.2 | 4.5 | 4.2 | 4.3 |
| SDS (0.01%) Nutrient cream containing composite compound (BASAM) (0.1%) [Preparation Example 1] | 3.9 | 3.6 | 3.2 | 3.57 |
| Nutrient cream containing composite compound (BASAM) (1%) [Preparation Example 2] | 2.1 | 1.8 | 1.8 | 1.9 |
| Nutrient cream containing composite compound (BASAM) (3%) [Preparation Example 3] | 0.66 | 0.63 | 0.57 | 0.62 |
| Nutrient cream containing composite compound (BASAM) (5%) [Preparation Example 4] | 0.66 | 0.57 | 0.57 | 0.60 |
| Nutrient cream containing no composite compound (0%) (BASAM) [Comparative Example] | 4.2 | 4.2 | 3.8 | 4.07 |

As shown in Table 8, when SDS (0.01%) was applied to the skin, average response degrees were calculated to be 4.3, demonstrating that the skin was severely damaged. Meanwhile, when each cream containing 0.1%, 1%, 3%, and 5% of the composite compound (BASAM) was applied, the skin was found to be protected depending on concentration. Accordingly, the composite compound (BASAM) was found to have the skin-protecting effect.

Example 9

Evaluation of Effect of Improving Atopic Dermatitis

The effect of improving atopic dermatitis was evaluated by a clinical test.

The nutrient creams prepared in Preparation Example (nutrient cream containing 3.0% composite compound, BASAM) and Comparative Example (nutrient cream containing purified water) were used.

The effect of improving atopic dermatitis was evaluated by EASI (Eczema Area Severity Index) score. 30 pediatric patients with atopic dermatitis were treated with the creams twice a day for 4 weeks and then, the effect of the composite compound (BASAM) on atopic symptoms was evaluated. Each EASI score was recorded at 0, 2, and 4 weeks after the treatment. The results are shown in FIG. 1.

Figure 1:
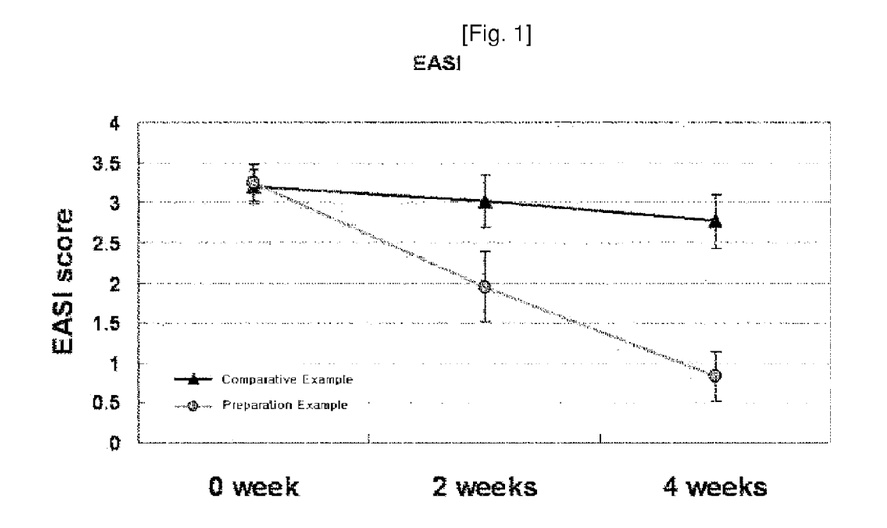
FIG. 1 is a graph showing the effect of improving atopic dermatitis by a nutrient cream containing 3.0% skin-protecting composition of the present invention (Preparation Example) and a nutrient cream containing purified water only (Comparative Example), in which the nutrient cream containing the skin-protecting composition of the present invention shows a significant effect of improving atopic dermatitis during the treatment period.

As shown in FIG. 1, the nutrient creams prepared in Preparation Example (nutrient cream containing 3.0% composite compound, BASAM) showed more excellent effect of improving atopic dermatitis than the nutrient creams prepared in Comparative Example (nutrient cream containing no composite compound, BASAM). It was found that the effect of improving atopic dermatitis increased, as treatment period increased.

INDUSTRIAL APPLICABILITY

A skin-protecting composition containing the composite compound of the present invention (BASAM) is a useful substance having all of excellent antioxidant, anti-inflammatory, wound-healing and moisturizing effects, thereby being widely used for protecting damaged skin. In particular, the skin-protecting composition is a complex of compounds derived from natural plants, and its various efficacies and safety for human skin were ensured. Accordingly, the composition can be used in medicine, cosmetic material or the like for the purpose of improving skin.

The invention claimed is:

1. A skin-protecting composition comprising glycyrrhizin, quercetin, rosmarinic acid, madecassic acid, chamazulene, baicalein and emodin, wherein said glycyrrhizin, quercetin, rosmarinic acid, madecassic acid, chamazulene, bicalein and emodin are contained in a weight ratio (g) of 1 to 2:2 to 5:0.5 to 1:0.5 to 1:1 to 2:1 to 2.

2. The skin-protecting composition according to claim 1, wherein glycyrrhizin, quercetin, rosmarinic acid, madecassic acid, chamazulene, baicalein and emodin are contained in a weight ratio of (g) of 1:2:0.5:0.5:1:1:1.

3. The skin-protecting composition according to claim 1, wherein glycyrrhizin, quercetin, rosmarinic acid, madecassic acid, chamazulene, baicalein and emodin are contained in an amount of 0.001 to 50 wt %, based on a total weight of the composition.

4. A pharmaceutical composition for treating atopic dermatitis, comprising the composition of claim 1 as an active ingredient.

5. A cosmetic material comprising the composition of claim 1 as an active ingredient.

6. The cosmetic material according to claim 5, wherein a formulation of the cosmetic material is a softening toner, a nutrient toner, a nutrient cream, a massage cream, an essence, an eye cream, a cleansing cream, a cleansing foam, a cleansing water, a pack, a spray, or a powder.

* * * * *